United States Patent [19]

Iori et al.

[11] 4,254,276

[45] Mar. 3, 1981

[54] PROCESS FOR THE PREPARATION OF PHENOLIC ETHERS

[75] Inventors: Giuseppe Iori; Ugo Romano, both of Milan, Italy

[73] Assignee: Anic, S.p.A., Palermo, Italy

[21] Appl. No.: 58,949

[22] Filed: Jul. 19, 1979

[30] Foreign Application Priority Data

Jul. 21, 1978 [IT] Italy ................ 25974 A/78

[51] Int. Cl.³ ............ C07C 41/16; C07C 41/01
[52] U.S. Cl. ............................ 560/64; 568/648; 568/650; 568/630
[58] Field of Search ............ 568/630, 648, 650; 560/70, 64

[56] References Cited

U.S. PATENT DOCUMENTS 2,529,887  11/1950  Smutz ................................. 568/630

FOREIGN PATENT DOCUMENTS

| 162 | 1/1979 | European Pat. Off. ............... 568/630 |
| 1048924 | 1/1959 | Fed. Rep. of Germany ........... 568/648 |
| 47-19785 | 6/1969 | Japan ................................... 568/630 |

Primary Examiner—Bernard Helfin
Attorney, Agent, or Firm—Morgan, Finnegan, Pine, Foley & Lee

[57] ABSTRACT

Phenolic ethers are prepared starting from phenol or a phenolic derivative and an alkyl carbonate which are reacted at a comparatively low temperature (below 160° C.) and with good yield and selectivity by using a catalytic system composed by a base, preferably a tertiary amine, and by an iodide, either organic or inorganic.

4 Claims, No Drawings

PROCESS FOR THE PREPARATION OF PHENOLIC ETHERS

This invention relates to a process for the preparation of phenolic ethers starting from a phenol or a derivative thereof and an alkyl ester of the carbonic acid, which are reacted in the presence of a catalytic system composed by a base and an iodide, organic or inorganic.

The importance is known of the phenolic ethers in the preparation of perfumes, due to their pleasant aroma and as antioxidants for alimentary oils and greases and stabilizers for plastics materials.

It is likewise known that, at present, such compounds are prepared by alkylating phenates with dialkylsulfates and thus by a procedure which provides for the use of an extremely toxic intermediate, which is the dialkylsulfate. In addition to this shortcoming the use of alkyl sulfate gives rise to the formation of sodium sulfate in a stoichiometric quantity relative to the ether sought for, and this makes it necessary to provide additional treatments for the waste waters in order to prevent environmental pollution. These defects are prevented by using, as the alkylating agents, the alkyl esters of carbonic acid, which alkylate the phenols and give, as by-products, alcohols and carbon dioxide which are not certainly pollutants. However, on account of the slower reactivity of the dialkyl carbonate relative to the dialkylsulfate, the reaction requires temperature conditions which are somewhat drastic in order that the reaction may take place at an acceptable reaction velocity. For example, the Japanese patent application No. 72-19785 by Asahi Chem., discloses the snythesis of anisole by methylation of sodium phenate with dimethylcarbonate at 240° C. for 5 hours.

At any rate, the methods known hitherto provide for the use of temperatures which are invariably above 160° C. in order that acceptable reaction velocities may be attained.

We have now found, and this is the subject matter of the present invention, that it is possible to carry out the reaction between phenols and alkyl esters of the carbonic acid under comparatively bland temperature conditions, i.e. below 160° C., the velocity remaining acceptable and the yields high.

The reaction takes place in the presence of a basic catalyst and of an appropriate promoter which is an iodide, either organic or inorganic.

The basic substance is preferably selected from among the aliphatic or aromatic, tertiary amines. Also the hydroxides of alkali metals and of alkaline earth metals show, in the presence of iodine-based promoters, an improved activity at a temperature below the temperatures reported by the literature.

The etherification reaction is carried out with stirring at 100° C.–150° C. under the spontaneously generated pressure, for a time of 2 to 6 hours consistently with the phenol which is used and the other reaction conditions which have been adopted.

On completion of the reaction, the mixture is separated by rectification, upon neutralization with an inorganic acid if an alkali was the used catalyst.

By way of example only, and without limitation, there are reported a few examples of the way of carrying out the reaction described herein.

EXAMPLE 1

A 100-ml stainless steel autoclave equipped with magnetic stirrer and immersed in an oil bath charged with 15 g (0.16 mol) of phenol, 32 g (0.35 mol) of dimethylcarbonate and 0.5 g of NaOH, The methylation reaction is carried out at 160° C. for 7 hours. A conversion of anisole of 20% is obtained, the selectivity being total.

EXAMPLE 2

The same apparatus as in Example 1 is charged with 15 g (0.16 mol) of phenol, 32 g (0.35 mol) of dimethylcarbonate, 0.4 g of NaOH and 0.1 g of KI. The methylation reaction is carried out for 2 hours at 150° C.

A conversion to anisole of 78% is obtained and the selectivity is total.

EXAMPLE 3

The apparatus of Example 1 is charged with 15 g of phenol, 32 g of dimethyl carbonate, 0.5 g of KOH and 0.8 g of KI.

The methylation reaction is carried out at 150° C. for 4 hours. The 60% of the phenol is converted to anisole and the selectivity is total.

EXAMPLE 4

The apparatus of Example 1 is charged with 15 g of phenol, 41 g of diethyl carbonate, 0.5 g of NaOH and 0.8 g of KI.

After 4 hours at 150° C. a conversion of 65% to phenetol is obtained, the selectivity being total.

EXAMPLE 5

The apparatus used in the previous Examples is charged with 15 g of phenol, 32 g of dimethyl carbonate, 0.9 g of N-methyl imidazole, The reaction conditions are 160° C. for 4 hours.

A conversion of phenol by 60% is obtained, with a total selectivity to anisole.

EXAMPLE 6

The apparatus of Example 1 is charged with 15 g of phenol, 32 g of dimethyl carbonate, 0.9 g of N-methylimidazole and 0.3 g of $CH_3I$. The reaction conditions are 150° C. for 3 hours.

The phenol is totally converted into anisol and the selectivity relative to anisole is total.

EXAMPLE 7

Under the same working conditions of Example 6, but by replacing $CH_3I$ by KI (0.4g) a total conversion of phenol is obtained, with a total selectivity relative to anisole.

EXAMPLE 8

The apparatus used in the previous Examples is charged with 23.1 g (0.21 mol) of hydroquinone, 45 g (0.5 mol) of dimethyl carbonate, 0.2 g of KI and 0.2 g of NaOH. After 2 hours of reaction at the temperature of 150° C., there is a conversion of 80% of the hydroquinone: of the converted quantity, the 70% is p.methoxyphenol and the 30% is 1,4-dimethoxybenzene. After 4 hours, a total conversion is experienced for the hydroquinone, the selectivity relative to 1,4-dimethoxybenzene being total.

EXAMPLE 9

The apparatus of the previous Examples is charged with 10.2 g of gallic acid (0.06 mol), 32.4 g of dimethyl carbonate (0.36 mol), 0.34 g of $CH_3I$ and 0.9 g of NMI.

After 2 hours at the temperature of 160° C. the gallic acid is entirely converted to 3,4,5-trimethoxy benzoate of methyl.

We claim:

1. A process for the preparation of phenolic ethers comprising reacting phenol or a derivative thereof with an alkyl ester of carbonic acid at a temperature of less than 160° C. in the presence of a catalytic amount of a base and an organic or inorganic iodide.

2. The process of claim 1 wherein said reaction is carried out at a temperature between about 100° C. and 150° C.

3. The process of claim 1 wherein said base is selected from the group consisting of aliphatic and aromatic tertiary amines and hydroxides of alkali metals and alkaline earth metals.

4. The process of claim 1 wherein said iodide is selected from methyl iodide and potassium iodide.

* * * * *